United States Patent [19]

Kühne et al.

[11] Patent Number: 4,851,222

[45] Date of Patent: Jul. 25, 1989

[54] METHOD OF PROMOTING REGENERATION OF BONE MARROW

[75] Inventors: Friedrich W. Kühne, Heidelberg; Stanislav Ivankovic, Neckargemuende, both of Fed. Rep. of Germany

[73] Assignee: Oxo Chemie GmbH, Fed. Rep. of Germany

[21] Appl. No.: 148,896

[22] Filed: Jan. 27, 1988

[51] Int. Cl.$^4$ ............................................. A61K 33/22
[52] U.S. Cl. .................................................... 424/661
[58] Field of Search ....................... 424/130, 127, 149

[56] References Cited

U.S. PATENT DOCUMENTS

| | | | |
|---|---|---|---|
| 4,507,285 | 3/1985 | Kuhne | 424/130 |
| 4,725,437 | 2/1988 | Kuhne | 424/149 |

FOREIGN PATENT DOCUMENTS

| | | |
|---|---|---|
| 3434982 | 4/1986 | Fed. Rep. of Germany . |
| 3515748 | 11/1986 | Fed. Rep. of Germany . |
| 3600931 | 7/1987 | Fed. Rep. of Germany . |

OTHER PUBLICATIONS

"Textbook of Medicine", Sixteenth edition, W. B. Sanders Company.
Elstner et al., "Heme Activation by Tetrachlorodecaoxide", CA 106:2751.
Youngman, "Time Kinetics of Hemoglobin and Myoglobin Activation by Tetrachlorodecaoxide", CA 105: 126,859.
Youngman et al., "Biochemical Oxygen Activation as the Basis for the Physiological Activation of Tetrachlorodecaoxide", CA 103: 64,427.

*Primary Examiner*—Douglas W. Robinson
*Assistant Examiner*—Roger Gobrogge
*Attorney, Agent, or Firm*—Wegner & Bretschneider

[57] ABSTRACT

In a process for promoting regenerating of bone marrow there is administered to a mammal in need thereof an effective regeneration promoting dose of an aqueous solution of stabilized oxygen in a matrix of chlorite ions.

3 Claims, 1 Drawing Sheet

METHOD OF PROMOTING REGENERATION OF BONE MARROW

The present invention relates to a method of promoting regeneration of damaged bone marrow. This objective is achieved by use of a composition consisting of a stabilized form of activated oxygen enclosed in a matrix of chlorite ions in an aqueous solution suitable for intravenous or intraperitoneal administration.

Such chlorite matrices with activate oxygen are disclosed in U.S. Pat. No. 4,507,285 as products of the formula $$ClO_2 \times nO_2$$

wherein n signifies the value of 0.1–0.25. In a preferred embodiment, n is about 0.21. Such chlorite matrix can be stabilized by oxygen or another element of Group VIa and b.

A preferred embodiment of the treatment of this invention employs administration of a mammal in need of bone marrow regeneration of an aqueous solution of a product which has become known as "tetrachlorodecaoxygen anion complex", commonly abbreviated as "TCDO", which is the product of Example 1 of U.S. Pat. No. 4,507,285. The product is a water clear liquid, miscible with alcohols, having a melting point of $-3°$ C. The Raman spectrum shows bands of 403, 802 (chlorite) and 1562 cm$^{-1}$ (activated oxygen).

It is an object of this invention to achieve bone marrow regeneration in mammals in which bone marrow damage has been produced by high levels of radiation, or by such other causes as mitogenic poisons or chemotherapy.

In the evaluation of the effect of TCDO in high dosage irradiation, it has been found that treatment with the matrix solution starting prior to commencement of radiation treatment or during the first three days of radiation sensitizes the animals to the effects of radiation, as evidenced by a higher mortality rate than that observed with saline treated controls. Unexpectedly, however, when TCDO treatment was delayed beyond the third day of exposure to radiation and continued thereafter, the effect was reversed and mortality decreased. A treatment regimen was developed accordingly based on the effect on bone marrow regeneration. In cases of severe bone marrow damage, a typical dosage regimen is currently suggested in higher mammals, especially in humans, starting on the fourth day after the onset of exposure to bone marrow damaging treatment such as radiation or chemical treatment.

The initial dosage typically uses 1 ml of a solution containing about 15.5 micromoles TCDO/Kg body weight per day for 2 days, followed by 7.75 micromoles/Kg for each of 4 days. In the case of prolonged radiotherapy or chemotherapy, treatment with 1-5 micromoles/Kg, typically about 3 micromoles daily may be used for periods of 3 months, depending on indications of bone marrow repair from the results of the blood examinations.

EXAMPLES

The following experiments were conducted in BD IX rats.

The mean lethal dose (LD$_{50}$) of TCDO in these animals was determined as 175.2 micromol/Kg intravenously. When daily intraperitoneal doses of up to 31 micromol/Kg were administered, no toxic effects were observed in the rats over a 2 year observation period.

TCDO, supplied by OXO Chemie, Heidelberg, FRG, was used in ready-to-use-solution containing 15.5 micromol/l in an isotonic, aqueous solution.

Animals:

In this rat strain, 15 Gray (Gy) was a 100% lethal dose of radiation. Radiation doses close to the LD$_{50}$ (11–11.5 Gy) were used in the following tests for evaluation of repeated injections of TCDO.

9-10 week old male BD IX rats[1] of 180± 10 g body weight were kept at standard condition at 23± 1° room temperature and 65% humidity, supplied with water and standard diet ad libitum. They were used at the age of 11–12 weeks and a weight of 320±20g.

[1]Rats obtained from the Zentralinstitut für Versuchstierzucht, Hanover.

Radiation:

Radiation was carried out with Siemens Gammatron S 80 (X-rays, Co-60) at a dose rate off 0.31 Gray (Gy)/min and a duration of radiation of 35.5 minutes; the animals underwent a single total-body irradiation with a total does of 11 Gy (1100 rd).

Test plan:

50 rats irradiated with 11 Gy and 50 non-irradiated animals were randomized into two groups each of 25 animals. One irradiated group and one non-irradiated group were treated with TCDO according to the following schedule: from day 4 after irradiation (or in the case of the non-irradiated animals, once the test had started), 15.5 micromol TCDO/ kg body weight (1 ml solution/kg) was administered intravenously once daily up to and including day 6. From day 7 to day 11 inclusive, the rats received half the dose (7.75 micromol TCDO/kg body weight) (0.5 ml/kg) once a day intravenously.

Another irradiated group only received physiological saline solution intravenously, in the same volume as the TCDO treated group and according to the same schedule (day 4–6: 1 ml/kg body weight per diem and day 7-11: 0.5 ml/kg body weight per diem).

Another group of non-irradiated animals remained untreated and served as control. Thus, there were four groups of animals:

Group I:
    25 irradiated (11 Gy) BD IX rats: from day 4 after irradiation, treatment with TCDO was administered according to the schedule above.

Group II:
    25 irradiated (11 Gy) animals: from day 4, intravenous administration of physiological saline solution (see above).

Group III:
    25 non-irradiated and untreated BD IX rats used as control.

Group IV:
    25 non-irradiated animals, which received TCDO intravenously according to the schedule as in Group I above.

Examinations:

For 40 days, including 4 weeks after treatment with TCDO was completed, the animals were controlled daily, moribund animals were recorded and post-mortem examinations were carried out immediately. Body weight was recorded daily during treatment and then every 3-4 days.

Analyses of the peripheral blood (erythrocyte and leucocyte counts, determination of hemoglobin values by means of a Coulter counter, and reticulocyte counts after brilliant cresyl blue staining) were made on day 0 (prior to irradiation), 3, 12 and 36. On day 12, an aspiration biopsy of the femur bone marrow was carried out under ether anesthesia on 6 animals in each group. The bone marrow was then examined cytologically after Giemsa staining.

All surviving animals were kept under observation until death for assessment for secondary chronic dosage.

RESULTS

Total body irradiation with 11 Gy caused 11 animals out of 25 which had only been treated with physiological saline (Group II) to die within 4 weeks after application was terminated. Actual causes of death were severe parenchymatous bleeding (mainly in the lungs and gastrointestinal tract) and intercurrent infections as a result of bone marrow aplasia. The mean survival time of the 11 animals was $21.3 \pm 10.4$ days. By contrast, in the group treated with TCDO (Group I), after the same irradiation dose and within the same period of observation, only one animal out of 25 died, of bronchial pneumonia. In FIG. 1 the death rates of both irradiated groups are shown. In groups III (non-irradiated and untreated controls) and IV (non-irradiated animals, which were treated with TCDO according to the schedule) there were no deaths.

Table 1 shows the most important hematological findings (erythrocyte, leucocyte, reticulocyte counts and the hemogrlobin content) in the peripheral blood of the animals in all 4 groups on day 0 (prior to irradiation, or at the start of the study), day 12 (end of treatment) and day 36. The initial values (day 0) of all animals in all groups were within normal limits for the animal strain used. In both irradiated groups (I and II) the mean leucocyte value on day 3 had dropped to $2.9 \times 10^3$ cells per microliter. Whereas on day 12 and 36 the number of leucocytes of the animals in group II had only risen to $3.5 \times 10^3$ or $4.9 \times 10^3$ per microliter respectively, the TCDOtreated group already showed signs of recovery with leucocyte values of $10.9 \times 10^3$ leucocytes/microliter on day 12, and $13.2 \times 10^3$ leucocytes/microliter on day 36. The differences in the erthyrocyte values of both irradiated groups were less pronounced during the observation period, however reticulocyte counts of ca. 3.1 (day 12) and 4.4 (day 36 per $10^3$ erythrocytes in the group treated only with physiological saline, pointed to severely disturbed erythropoiesis, while values of ca. 9.8 per $10^3$ Er (day 12) and 11.2 per $10^3$ Er (day 26) in the TCDO-treated animals already gave evidence of erythrocyte formation returning to normal. The TCDO-group also came off better in the hemoglobin content.

TABLE I

Hematological Parameters in the Peripheral Blood

| t: (days) | Parameters: (units) | I (11 Gy + TCDO) $\bar{x}$ | SD | II (11 Gy + NaCl) $\bar{x}$ | SD | III (control group) $\bar{x}$ | SD | IV (TCDO) $\bar{x}$ | SD |
|---|---|---|---|---|---|---|---|---|---|
| 0 | Er ($\times 10^6/\mu l$) | 8,4 | ± 0,3 | 8,8 | ± 0,3 | 8,2 | ± 0,4 | 8,6 | ± 0,4 |
|   | Leuco ($\times 10^3/\mu l$) | 17,0 | ± 1,7 | 16,7 | ± 1,4 | 18,2 | ± 2,5 | 19,2 | ± 1,8 |
|   | Hb (g/100 ml) | 16,2 | ± 0,9 | 16,6 | ± 0,8 | 16,6 | ± 0,7 | 16,3 | ± 0,5 |
|   | Reticulo (/$10^3$Er) | 15,4 | ± 4,1 | 12,2 | ± 3,5 | 13,6 | ± 3,0 | 11,7 | ± 4,2 |
| 12 | Er ($\times 10^6/\mu l$) | 6,9 | ± 0,6 | 5,6 | ± 0,4 | 7,9 | ± 0,7 | 7,1 | ± 0,2 |
|   | Leuco ($\times 10^3/\mu l$) | 10,9 | ± 1,6 | 3,5 | ± 0,4 | 19,8 | ± 2,7 | 15,8 | ± 1,8 |
|   | Hb (g/100 ml) | 14,4 | ± 0,7 | 7,4 | ± 0,3 | 16,9 | ± 0,3 | 15,6 | ± 0,5 |
|   | Reticulo (/$10^3$Er) | 9,8 | ± 0,9 | 3,1 | ± 0,4 | 14,3 | ± 2,0 | 64,5 | ± 7,0 |
| 36 | Er ($\times 10^6/\mu l$) | 7,8 | ± 0,4 | 5,9 | ± 0,7 | 8,8 | ± 0,7 | 8,0 | ± 0,3 |
|   | Leuco ($\times 10^3/\mu l$) | 13,2 | ± 2,0 | 4,9 | ± 1,6 | 17,9 | ± 2,2 | 19,8 | ± 2,0 |
|   | Hb (g/100 ml) | 15,9 | ± 0,4 | 10,1 | ± 0,4 | 16,0 | ± 0,4 | 15,8 | ± 0,8 |
|   | Reticulo (/$10^3$Er) | 11,2 | ± 3,0 | 4,4 | ± 0,8 | 12,8 | ± 2,6 | 14,3 | ± 2,0 | t = time after irradiation;
$\bar{x}$ = mean values;
SD = standard deviation

The data relating to group III (non-irradiated and untreated animals) served as reference values. At the end of TCDO-administration (day 12), group IV showed a minimal drop in erythrocyte and Hb values; at a level of 64.5 per $10^3$ Er however there was reticulocytosis. (In previous toxicity studies there have been observed a marked hemolysis with an increase in bilirubin and urobilinogen when TCDO was administered repeatedly in high doses over 31 micromol/kg b.w.). On day 36 all blood values in this group were within the norm.

A comparison of the bone marrow findings from group I and group II on day 12 after aspiration from the femur and hematoylin-eosin-staining showed the following results. The bone marrow of the animal in group II showed very few cells. Most cells showed pyknotic alteration of the nucleus. The chromatin was condensed and shifted to the border of the nucleus. The cytoplasm was often vacuolated. The bone marrow of the TCDO-treated animals showed lively cell-proliferation (active erythropoiesis and myelopoiesis) and regeneration. Cells of normal structure and mature granulocytes were already present.

The body weight curves of the animals in both of the irradiated groups showed no significant differences; with an average weight loss of circa 20%, the lowest point was reached on day 5 and then both groups regained their initial weight again almost simultaneously. The body weight of the animals in group IV followed the same course as that of the non-irradiated and untreated control group.

The data show that TCDO reduces considerably the acutely lethal effect on high radiation dosage. It promotes the regeneration of bone-marrow which in turn causes the hemogram to return to normal.

Figure 1:
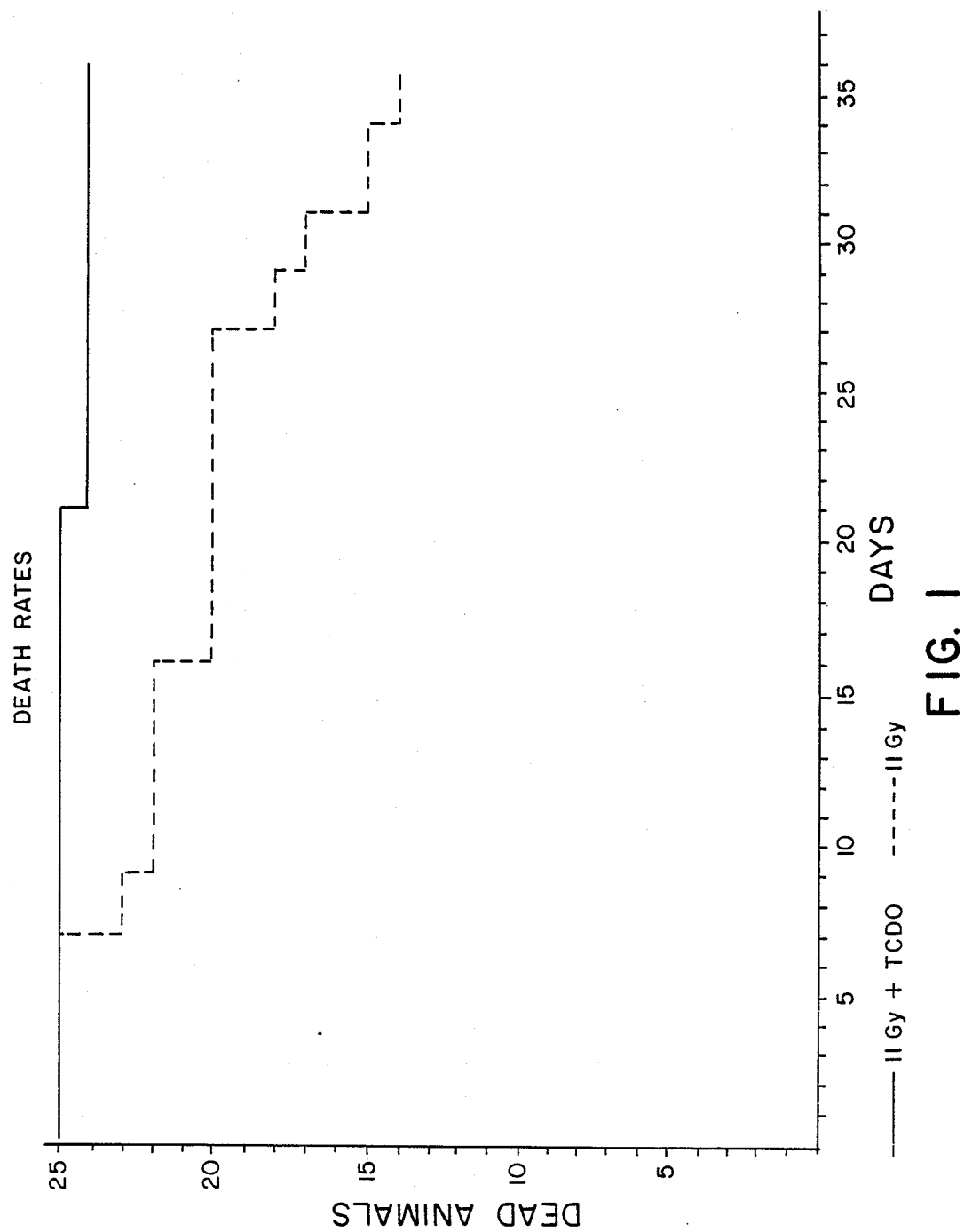
FIG. 1 presents a comparison of the death rates in group I (solid line) and group II (broken line) after whole-body irradiation with 11 Gy. It was noted that in the TCDO-treated with saline solution, 11 out of 25 died within the same observation period.

What is claimed is:

1. Process for promoting regeneration of bone marrow wherein there is injected into a mammal in need thereof an effective regeneration promoting dose of an aqueous solution of stabilized activated oxygen in a matrix of chlorite ions of the formula $ClO_2 \times nO_2$, wherein n is 0.1–0.25.

2. Process of claim 1 wherein the stabilized, activated oxygen matrix is TCDO and an effective dose is injected intravenously.

3. Process for promoting regeneration of bone marrow damaged by radiation wherein an effective regeneration promoting dose of TCDO is injected more than 3 days after first exposure to radiation.

* * * * *